(12) United States Patent
Krebs-Bensch

(10) Patent No.: US 11,478,420 B1
(45) Date of Patent: *Oct. 25, 2022

(54) VAGINAL PROBIOTIC PRODUCTS AND RELATED PROCESSES

(71) Applicant: Grace Procurements LLC, Decatur, GA (US)

(72) Inventor: Allison Krebs-Bensch, Decatur, GA (US)

(73) Assignee: Grace Procurements LLC, Decatur, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/079,869

(22) Filed: Oct. 26, 2020

Related U.S. Application Data

(63) Continuation of application No. 16/294,421, filed on Mar. 6, 2019, now Pat. No. 10,842,737, which is a continuation of application No. 15/815,837, filed on Nov. 1, 2017, now Pat. No. 10,258,567.

(60) Provisional application No. 62/423,539, filed on Nov. 17, 2016.

(51) Int. Cl.
| | | |
|---|---|---|
| A61K 35/747 | (2015.01) | |
| A61K 9/00 | (2006.01) | |
| A61K 9/48 | (2006.01) | |
| A61K 47/36 | (2006.01) | |
| A61K 31/355 | (2006.01) | |
| A61K 33/22 | (2006.01) | |
| A61K 31/341 | (2006.01) | |

(52) U.S. Cl.
CPC .......... *A61K 9/0034* (2013.01); *A61K 9/4833* (2013.01); *A61K 9/4866* (2013.01); *A61K 31/341* (2013.01); *A61K 31/355* (2013.01); *A61K 33/22* (2013.01); *A61K 35/747* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,324,515 A | 6/1994 | Lee et al. | |
| 6,761,885 B1 | 7/2004 | Hakansson et al. | |
| 6,797,266 B2 | 9/2004 | Naidu | |
| 7,214,370 B2 | 5/2007 | Naidu | |
| 7,507,402 B1 | 3/2009 | Farmer et al. | |
| 7,510,734 B2 | 3/2009 | Sullivan et al. | |
| 8,048,456 B2 | 11/2011 | Burke-Colvin et al. | |
| 8,114,658 B2 | 2/2012 | Muroyama et al. | |
| 8,481,299 B2 | 7/2013 | Gueniche | |
| 8,846,082 B2 | 9/2014 | Baksh | |
| 8,895,060 B2 | 11/2014 | Baksh | |
| 9,011,902 B2 | 4/2015 | Di Schiena | |
| 10,258,567 B1 * | 4/2019 | Krebs-Bensch | A61P 15/02 |
| 10,842,737 B1 * | 11/2020 | Krebs-Bensch | A61K 35/747 |
| 2010/0226892 A1 | 9/2010 | Gueniche | |
| 2011/0182861 A1 | 7/2011 | Castiel et al. | |
| 2012/0156171 A1 | 6/2012 | Breton et al. | |
| 2012/0301453 A1 | 11/2012 | Minea et al. | |
| 2013/0101576 A1 | 4/2013 | Rao et al. | |
| 2014/0369982 A1 | 12/2014 | Naidu | |

FOREIGN PATENT DOCUMENTS

| | | |
|---|---|---|
| WO | 9729762 | 8/1997 |
| WO | 0228402 | 4/2002 |
| WO | 02058712 | 6/2003 |
| WO | 2004028460 | 6/2004 |
| WO | 2015173693 | 11/2015 |

OTHER PUBLICATIONS

"Douching Fact Sheet", Available Online at: https://www.womenshealth.gov/a-z-topics/douching, ePublications, Our ePublications, Accessed from internet on Mar. 5, 2018, 4 pages.

"EcoVag Balance", FrezyDerm, Available Online at: hhtps://www.frazyderm.com/en/intimate-area/intravaginal-care/ecovag-balance-/, Accessed from internet on Nov. 24, 2015, pp. 1-3.

"Gy-Na-Tren Description", Natren Inc., Apr. 2012, 4 pages.

"Gy-Na-Tren Dual Action Vaginal Health Kit", Vitacost, Available Online at: http://www.vitaost.com/natren-gy-na-tren-dual-action-vaginal-health-Kit-2-bottles, Nov. 24, 2015, pp. 1-3.

"HylafemTM Homeopathic Rx Vaginal Suppositories", Available Online at https://dailymed.nlm.nih.gov/dailymed/archives/fdaDrugInfo.cfm?archiveid=198663, Mar. 10, 2016, pp. 1-6.

"Material Specification Sheet", ProbioFerm, Composition: Dried Lactobacillus casei fermentation culture 50-60%, Maltodextrin 40-50%, Silica 1 %, Description of the product offered for sale before Apr. 18, 2016., 1 page.

"Treatment of Bacterial Vaginosis Using Probiotics", Available Online at: http://www.powerofprobiotics.com/Treatment-of-bacterial-vaginosis-using-probiotics.html, Nov. 24, 2015, pp. 1-9.

"Vaginal Infections (Vaginitis)", Center for Young Women's Health, Internet Page, Available Online at: http://youngwomenshealth.org/2012/11/20/vaginal-infection/, Nov. 20, 2012, 2 pages.

"Vaginal pH Balance", Available Online at: Just-Health.net, Accessed from internet on Mar. 5, 2018, 2 pages.

U.S. Appl. No. 15/815,837, Non-Final Office Action, dated Apr. 16, 2018, 18 pages.

U.S. Appl. No. 15/815,837, Notice of Allowance, dated Dec. 5, 2018, 7 pages.

U.S. Appl. No. 15/815,837, "Restriction Requirement", dated Feb. 12, 2018, 8 pages.

U.S. Appl. No. 16/294,421, Non-Final Office Action, dated Jun. 19, 2020, 7 pages.

(Continued)

*Primary Examiner* — Vera Afremova

(74) *Attorney, Agent, or Firm* — Kilpatrick Townsend & Stockton LLP

(57) ABSTRACT

A formulation for vaginal administration comprising an effective amount of a composition of dried *Lactobacillus* cells and boric acid, with a carrier. The composition can include one or more antioxidants. Optionally, the composition is in a unit dosage form. Also provided are methods for making and using the composition.

20 Claims, No Drawings

(56) References Cited

OTHER PUBLICATIONS

U.S. Appl. No. 16/294,421, Notice of Allowance, dated Jul. 24, 2020, 7 pages.

Cribby et al., "Vaginal Microbiota and the Use of Probiotics", Interdisciplinary Perspectives on Infectious Diseases, vol. 2008, Article ID 256490, 2008, pp. 1-9.

Dover et al., "Natural Antimicrobials and Their Role in Vaginal Health: A Short Review", Int. J Probiotics-Prebiotics, vol. 3, No. 4, 2008, pp. 219-230.

Gueniche et al., "Lactobacillus Paracasei CNCM 1-2116 (ST11) Inhibits Substance P-Induced Skin Inflammation and Accelerates Skin Barrier Function Recovery in Vitro", Eur. J Dermatol., vol. 20, No. 6, Oct. 7, 2010, 1 page.

Hagino et al., "Lactobacillus Casei KE-99 Action to Improve Skin Condition", Fragrance Journal, May 5, 2014, 7 pages.

Larsson et al., "Extended Antimicrobial Treatment of Bacterial Vaginosis Combined with Human Lactobacilli to Find the Best Treatment and Minimize the Risk of Relapses", BMC Infectious Diseases, vol. 11, No. 223, 2011, pp. 1-14.

Muizzuddin et al., "Effect of Lactobacillus Extract on Acne", J. Invest. Dermatol., Available Online at: http://toolkit.dialog.com/intranet/cgi/present?STYLE=1360084482&PRESENT=DB=73,AN+86501036,FM=, Apr. 1, 2011, 1 page.

Muizzuddin et al., "Physiological Effect of a Probiotic on Skin", J. Cosmet. Sci., vol. 63, No. 6, Nov.-Dec. 2012, 1 page.

Prutting et al., "Boric Acid Vaginal Suppositories: A Brief Review", Infectious Diseases in Obstetrics and Gynecology, vol. 6, Aug. 19, 1998, pp. 191-194.

ROTARANGI , "Vaginal pH—Everything You Need to Know", Available Online at: http://www.probiotics-lovethatbug.com/vaginal-ph.html, Accessed from internet on Mar. 5, 2018, 5 pages.

Simmering et al., "Pre-and Probiotic Cosmetics", Hautarzt, vol. 60, No. 10, Available Online at: https://link.springer.com/article/10.1007/s00105-009-1759-4, Oct. 2009, pp. 809-814.

Sultana et al., "Lysates of Lactobacillus and Bifidobacterium Augment Tight Junction Barrier Function in Human Primary Epidermal Keratinocytes in a Strain-Dependent Manner", Applied and Environmental Microbiology, vol. 79, No. 16, Available Online at: http://aem.asm.org/content/early/2013/06/03/AEM.00982-13.short, 2013, 1 page.

Volz et al., "Outside-In", Probiotic topical agents, Hautarzt, vol. 60, No. 795, Available Online at: https://link.springer.com/article/10.1007%2Fs00105-009-1755-87LI=true, Oct. 2009, pp. 1-8.

\* cited by examiner

VAGINAL PROBIOTIC PRODUCTS AND RELATED PROCESSES

PRIOR RELATED APPLICATIONS

This application is a continuation of U.S. patent application Ser. No. 16/294,421, filed Mar. 6, 2019, which is a continuation of U.S. patent application Ser. No. 15/815,837, filed Nov. 17, 2017, now U.S. Pat. No. 10,258,567, issued Apr. 16, 2019, which claims the benefit of U.S. Provisional Application No. 62/423,539, filed Nov. 17, 2016. The foregoing applications are incorporated herein by reference in their entirety.

FIELD

The invention is related to vaginal probiotic products and processes of making and using such products.

BACKGROUND

Urogenital infections and inflammatory conditions of various origins are experienced by many females throughout their lives. One example of such a condition is vaginitis, which is characterized in the medical field as an inflammation of the vulvovaginal region. Vaginitis includes the conditions associated with a perturbation in the composition of the normal vaginal microflora. Such perturbation may involve depletion of lactobacilli species and overgrowth of other bacterial species, such as *Gardnerella vaginalis* and obligate anaerobes, resulting in bacterial vaginosis (BV). Candidal vaginitis is typically caused by overgrowth of *Candida* yeast, most commonly overgrowth of commensal fungal organism *Candida albicans*. Vaginitis symptoms may include change in color, odor or amount of discharge from a subject's vagina, vaginal itching or irritation, pain during intercourse, painful urination, and light vaginal bleeding or spotting. Vaginitis can lead to various degrees of discomfort and can lower the overall quality of life. Vaginitis can also have serious medical consequences. For example, BV may increase the risk of HIV acquisition, premature labor in pregnant subjects and low birth weight in their babies. Vaginitis therefore should be promptly treated to improve the quality of life and to avoid medical complications. Urogenital infections are typically treated with various antimicrobial treatments, including antibiotics and antifungal agents, but the recurrence rate is high and side effects are common. Improved compositions and methods for treatment, alleviation or prevention of urogenital infections and inflammation are desirable.

SUMMARY

Described herein are vaginal probiotic products useful for treating or preventing urogenital infections and inflammatory conditions, including vaginitis, and processes for making and using such products. For example, a formulation for vaginal administration is provided that contains an effective amount of a composition including dried viable *Lactobacillus* cells (e.g., one or more of *Lactobacillus casei*, *Lactobacillus gasseri* or *Lactobacillus acidophilus*, such as a combination of *Lactobacillus casei* and *Lactobacillus gasseri* JPS), boric acid, one or more antioxidants (e.g., vitamin E and/or vitamin C) and a carrier (e.g., maltodextrin). The formulation can be in a capsule unit dosage form.

An exemplary method of making the formulations include the steps of triturating boric acid with a first amount of a carrier, thereby resulting in triturated boric acid having about 1-3% (for example, 1%, 2% or 3%) boric acid by weight, and blending dried viable *Lactobacillus* cells with a second amount of the carrier and one or more antioxidants to produce a probiotic blend. An amount of the probiotic blend is then blended with an amount of the triturated boric acid to produce a mixture comprising dried viable *Lactobacillus* cells, the triturated boric acid, the one or more antioxidants and the carrier.

Also provided herein is a method of treating a urogenital infection or inflammatory condition (e.g., vaginitis) in a subject by intravaginally or transvaginally administering to the female subject the formulation including dried viable *Lactobacillus* cells, boric acid, one or more antioxidants and a carrier.

This summary is a high-level overview of various aspects of the invention and introduces some of the concepts that are further described in the Detailed Description section below. This summary is neither intended to identify key or essential features of the claimed subject matter nor intended to be used in isolation to determine the scope of the claimed subject matter. The subject matter should be understood by reference to appropriate portions of the entire specification and each claim.

Other objects and advantages of the invention will be apparent from the following detailed description of embodiments of the invention.

DETAILED DESCRIPTION

Formulations

Embodiments of the present products and formulations include probiotic vaginal formulations, which are useful for treating, preventing or reducing one or more symptoms of a urogenital infection or inflammatory condition or alleviating urogenital infections or inflammatory conditions. For example, probiotic vaginal formulations described herein may relieve symptoms of vaginitis, such as internal and external vaginal burning, itching, and irritation, and may reduce vaginal foul odor. An exemplary but non-limiting embodiment of a formulation for vaginal administration contains, in a soluble capsule, dried viable cells of *Lactobacillus*, boric acid and a carrier.

Dried viable cells of *Lactobacillus* are the probiotic component of the probiotic vaginal formulation. *Lactobacillus* cells are included in the probiotic vaginal formulations in order to beneficially influence vaginal health. Dried *Lactobacillus* cells may include dried cells of *L. acidophilus*, *L. casei*, *L. gasseri* (e.g., strain *L. gasseri* JPS), or a combination thereof. In an exemplary embodiment, dried *L. casei* cells are the cells of *L. casei* PTA-3945. Optionally, a combination of dried cells of *L. casei* PTA-3945 and dried cells of *L. gasseri* JPS cells is used. Dried *Lactobacillus* cells as used herein are viable and are capable of growing in the urogenital system (e.g., the vaginal cavity) of the subject upon administration.

The mechanisms by which Lactobacilli probiotics beneficially affect vaginal health are not fully understood. These mechanisms may involve production of antimicrobial factors, creation and maintenance of low vaginal pH, reduction of the ability of a wide range of pathogens to adhere, for example, by coaggregation of some pathogens or production of surfactants, or killing of the pathogens through production of antimicrobial agents. *Lactobacillus* cells administered with the probiotic vaginal formulations may temporarily populate vaginal cavity and create an environment favorable for restoration of normal vaginal flora and unfavorable for the return of pathogens. *Lactobacillus* cells administered with the probiotic vaginal formulations may also prevent the spread of pathogens, such as the transfer of pathogens from the rectal area to the urogenital system, or the infection of the urogenital system by sexually transmitted pathogens, thus preventing or reducing the likelihood of occurrence of urogenital infections in the subjects. One possible mechanism for this beneficial effect is the known ability of Lactobacilli to produce bacteriocins, which can inhibit the growth of certain bacteria associated with BV, such as *G. vaginalis*. Lactobacilli can also produce other antimicrobial compounds, such as hydrogen peroxide (produced by *L. gasseri*), and weak organic acids, for example, lactic and acetic acids, which lower the vaginal pH. Lactobacilli ferment glycogen secreted by the vaginal epithelial cells into lactic acid, and colonization by Lactobacilli correlates with the acidity of the vaginal fluid. Low vaginal pH (normal range of about 3.8 to 4.5) is thought to protect the vulvovaginal environment from overgrowth of yeast and some pathogenic organisms. The embodiments described herein are not limited by any the above mechanisms, and different mechanisms of advantageous probiotic actions of Lactobacilli may occur.

An exemplary embodiment of probiotic vaginal formulations described herein contains a combination of dried viable cells of *Lactobacillus casei* PTA-3945 and *Lactobacillus gasseri* JPS. The combination of dried viable cells of *Lactobacillus casei* PTA-3945 and *Lactobacillus gasseri* JPS is unexpectedly effective for maintenance and/or restoration of vaginal health, treatment and/or relief of the symptoms of urogenital infections, and/or reduction of occurrence of urogenital infections.

Exemplary probiotic vaginal formulations according to the embodiments of the present invention comprise approximately 1.8-3.3 billion, 1.8-2.7 billion, 1.8-2.2 billion, 2.2-2.7 billion, 2.2-3.3 billion or 2.2-2.7 billion colony forming units (CFU) of *L. casei*, such as *L. casei* PTA-3945, per unit dosage form. Exemplary probiotic vaginal formulations according to the embodiments of the present invention comprise approximately 0.9-2.2 billion, 0.9-1.1 billion, 0-9-1.8 billion, 1.1-1.8 billion or 1.1-2.2 billion CFU of *L. gasseri*, such as *L. gasseri* JPS, per unit dosage form.

The probiotic vaginal formulations described herein include boric acid. When vaginally administered, boric acid is a bacteriostatic and fungistatic agent. Boric acid activity upon administration into vaginal cavity may be mediated by acidification of the vaginal environment, but other mechanisms of action may result in the advantageous properties of boric acid. Higher than normal pH (i.e., greater than about 3.8 to 4.5) is associated with disruptions in bacterial flora and overgrowth of undesirable microorganisms. Boric acid may also penetrate the cell walls and disrupts the cell membranes of fungi and other pathogens by inhibiting the ergosterol synthesis. Some embodiments of the vaginal probiotic formulations described herein contain boric acid subjected to a homeopathic trituration procedure, described in more detail elsewhere herein. Some embodiments contain boric acid, in a specified amount or concentration, without homeopathic trituration. The concentrations of the boric acid used in the probiotic vaginal are selected to exert the beneficial effect while avoiding vaginal irritation. In some embodiments of probiotic vaginal formulations, the concentrations of the boric acid are used that can be described as "homeopathic" and fall within the practices of homeopathy system. An advantage of such homeopathic formulations is that they are acceptable for and can be used by the adherents to homeopathy system. Some examples of the probiotic vaginal formulations contain about 0.0059-0.0072% by weight of boric acid (excluding the weight of the capsule in the capsule unit dosage form embodiment), about 0.025 mg of boric acid per unit dosage form, and can contain of up to 600 mg of boric acid per unit dosage form.

The probiotic vaginal formulations described herein include a carrier. A carrier acts as a filler or a bulking agent and optimizes the preparation, the storage and/or the delivery of the probiotic vaginal formulations. For example, a carrier can ease the handling of the of the formulation by facilitating its flowability and simplifying the measuring of the ingredients, particularly those used in low amounts or concentrations, such as boric acid. A carrier can also prevent aggregation of the formulation and ensure stability during storage. Certain carries are unsuitable for the probiotic vaginal formulations, because they serve as food sources for Lactobacilli. For example, the use of lactose as a carrier may lead to reconstitution and premature multiplication of the probiotics during storage, which may reduce viability (or increase degradation) of the probiotics and may promote premature disintegration of the unit dosage form (for example, capsule rupture). One example of a suitable carrier is maltodextrin, as it does not serve as a food source for Lactobacilli. The probiotic vaginal formulations contain approximately 37-47% by weight of a carrier. For example, certain embodiments of the probiotic vaginal formulation can contain 30-55%, 35-50%, or 37-47% by weight of maltodextrin, excluding the weight of the capsule in the capsule unit dosage form embodiment. The carrier weight % described herein may exclude the weight of a carrier, such as maltodextrin, supplied through some components of the formulation. For example, some carrier, such as maltodextrin, may be included in the probiotic components by their supplier—it may be not taken into account in the above weight percentages.

The probiotic vaginal formulations described herein may contain one or more antioxidants. The antioxidants play a role in preserving the formulation by preventing the oxidation of its components and may play other beneficial roles. Examples of suitable antioxidants are vitamin C and E. Vitamin C, when incorporated in the formulation in the form of ascorbic acid, serves as a preservative and also helps to reduce vaginal pH upon administration of the formulation. Vitamin E may act as a preservative and may also have an anti-inflammatory effect on the vaginal tissues. In certain embodiments of the probiotic vaginal formulations, vitamin E is included as DL-alpha-tocopheryl acetate. Since DL-alpha-tocopheryl acetate is normally a liquid at room temperature, it may be used in a microencapsulated form. Probiotic vaginal formulations optionally comprise about 5-25%, 10-20%, or 11-15% ascorbic acid by weight (excluding the weight of the capsule in the capsule unit dosage form embodiment). For example, about 13% ascorbic acid by weight is optionally used. Probiotic vaginal formulations can comprise about 10-30%, 15-25%, or 17-22% vitamin E by weight (excluding the weight of the capsule in the capsule unit dosage form embodiment), which may be provided as DL-alpha-tocopheryl acetate. A microencapsulated form of DL-alpha-tocopheryl acetate containing about 50% of DL-alpha-tocopheryl acetate by weight may be used as a starting material.

The probiotic vaginal formulations can also contain various other components, in addition to those described above. Non-limiting examples of such additional components are desintegrants, preservatives, dyes, fragrances or natural extracts, such as plant extracts. Some examples of additional ingredients are guar gum, citric acid and/or aloe vera extract in powdered form. For example, some embodiments of the probiotic vaginal formulations can contain 50-150 mg of aloe vera extract per unit dosage form. Some other non-limiting examples of additional components are non-viable bacterial cells, disrupted bacterial cells, bacterial cell debris or fragments, stand-alone components of bacterial cells (such as biological molecules or their complexes) and products of bacterial cell breakdown. For example, the probiotic vaginal formulations can contain non-viable *Lactobacillus* cells, disrupted *Lactobacillus* cells, *Lactobacillus* cell debris and fragments, stand-alone components of *Lactobacillus* cells and products of *Lactobacillus* cell breakdown. The above examples of additional components can originate from *Lactobacillus casei, Lactobacillus* gasseri or *Lactobacillus acidophilus* cells. Probiotic vaginal formulations can contain bacterial metabolites, such as the products and intermediates of growth and metabolism of *Lactobacillus* bacteria (such as *Lactobacillus casei, Lactobacillus* gasseri or *Lactobacillus acidophilus*) in culture. In one example, the probiotic vaginal formulations can contain a component prepared from the growth media in which bacterial cells, such as *Lactobacillus* cells, were cultured. Such a component can contain one or more of non-viable bacterial cells, disrupted bacterial cells, bacterial cell debris or fragments, bacterial cell components, products of bacterial cell breakdown and bacterial metabolites. The exemplary component can be referred to as "growth media," "growth media extract," "dried growth media," etc. In another example, the probiotic vaginal formulations can contain a component prepared from cultured bacterial cells, such as *Lactobacillus* cells. Such a component can contain one or more of non-viable bacterial cells, disrupted bacterial cells, bacterial cell debris or fragments, bacterial cell components, products of bacterial cell breakdown and bacterial metabolites. The exemplary component can be referred to as "cell extract," "cell fragments," etc. The above exemplary components, while not limited by any production process, can be obtained from the starting materials (such as bacterial culture or cultured bacterial cells) by methods that involve, in various combinations, disruption of bacterial cells (for example, by sonication or high pressure homogenization), heating steps, suitable drying processes, such as freeze-drying, spray-drying, or drying under vacuum, separation steps (such as filtration or centrifugation), etc.

The dosage forms of the probiotic vaginal probiotic formulations are suitable for vaginal administration and are selected to deliver an effective amount of the vaginal probiotic formulation. In some embodiments, the probiotic vaginal formulation is supplied as a powder and can be administered by a suitable applicator. In this case, the probiotic vaginal formulation may be supplied as a component of a kit, which includes an applicator. The probiotic vaginal formulation may be pre-packaged in the applicator, or supplied as a separate item of the kit. In some other embodiments, the probiotic vaginal application are incorporated into vaginal tampons. A kit comprising the tampons optionally includes one or more applicators. Suitable dosage forms also include vaginal suppositories, including capsules and tablets, which can be administered by with or without a suitable applicator. The choice of the dosage form depends on a variety of factors. For example, the chosen dosage form should ensure stability of the formulation's ingredients during storage, convenient administration and quick delivery of the formulation in the vaginal environment. In particular, the dosage form of the probiotic vaginal formulations should not detrimentally affect viability or allow premature (prior to administration) reconstitution of the probiotic components of the formulation. To this end, the dosage form should not contain water. At the same time, the dosage form should allow for quick dispersion or dissolution of the formulation's ingredients in the vaginal environment upon administration. For example, if a tablet or a capsule is chosen as a dosage form, it should be formulated to disintegrate quickly when administered into vagina.

As discussed above, in some embodiments, the probiotic vaginal formulations are in a capsule unit dosage form. The capsule unit dosage form allows for stability during storage by protecting the content of the capsule from moisture, which can lead to premature reconstitution of the probiotic component of the formulations, and other environmental factors that can be detrimental to the stability of the formulations. At the same time, the capsules employed in a capsule unit dosage form of the probiotic vaginal formulations should be suitable for vaginal administration. For example, they are selected to be non-irritating in a vaginal environment, to be easy to administer and to dissolve quickly upon administration. As an example, a capsule comprising pullulan as a structural polymer component is used, but other types of capsules may also be suitable. Pullulan-based capsules are stable during storage, ensuring stability of the probiotic vaginal formulation ingredients. The pullulan-based capsules do not irritate vulval and vaginal tissues upon administration and disintegrate quickly in the vaginal environment, resulting in quick delivery of the formulation ingredients after the capsule is administered. Also, pullulan solutions are viscous, which ensures improved retention of the probiotic formulation ingredients in the vaginal cavity. The size and the shape of the capsules used in the capsule unit dosage forms of the probiotic vaginal formulations are chosen for convenient vaginal administration, including, for example, self-administration by the subject.

Each unit dosage form contains an effective amount of the probiotic vaginal formulation. The amount of the vaginal formulation included in the unit dosage form depends on a variety of factors, such as the concentration of the active ingredients (the active ingredients may be the probiotic component and/or the boric acid component), the rate of release upon administration, the age and health of the subject, the severity of the urogenital infection or inflammatory condition, the convenience of administering the formulation, and the like. For example, some unit dosage forms, such as the capsule unit dosage form, of the probiotic vaginal formulations contain about 100-1000 mg of the probiotic vagina formulation, such as about 100 mg, about 200 mg, about 300 mg, about 400 mg (for example, 380 mg), about 500 mg, about 600 mg, about 700 mg, about 800 mg, about 900 mg or about 1000 mg.

Processes for Making the Formulations

Processes (methods) for making or preparing probiotic vaginal formulations are also provided herein. In some embodiments, the ingredients of the probiotic vaginal formulations, which can be obtained from commercial sources or produced, are combined according to the standard formulation procedures adopted in the field of pharmaceutical production, food supplement production and the related fields. Standard formulation procedures can be modified as discussed below.

In some embodiments of the processes for preparing the probiotic vaginal formulation, boric acid, prior to being mixed with other ingredients of the probiotic vaginal formulation, is subjected to a trituration procedure to produce a fine powder containing boric acid and a carrier. Such powder can be described as "triturated boric acid." Triturated boric acid used in some embodiments contains about 1-3% of boric acid by weigh, for example, about 1%, about 2% or about 3% by weight. In some embodiments, triturated boric can be described as "homeopathic" and falls within the practices of homeopathy system. Trituration of boric acid is accomplished by milling (such as ball-milling), grinding, crushing or similar processes, which can be conducted over a specified time period, for example, about 1-10 hours. Trituration results in a mixture of boric acid and a carrier (such as maltodextrin), in which the particle size of the boric acid is reduced, as compared to the starting particle size. In other words, the trituration procedure of boric acid ensures small boric acid particle size. Accordingly, the manufacturing processes can include one or more steps of "triturating," "grinding," "blending," "mixing" or similar steps for mixing boric acid and the carrier. In some other embodiments, the small particle size of boric acid particles can be achieved by other, non-homeopathic processes.

A small particle size of boric acid particles ensures that boric acid readily dissolves in the vaginal cavity, quickly lowering vaginal pH. Small particle size of boric acid particles and dilution with a carrier also reduces the chance of creating local high concentrations of boric acid in vaginal environment, thus minimizing the changes of vaginal irritation. In an exemplary trituration procedure, boric acid and carrier, such as maltodextrin, are mixed in a specified ratio (for example 1 part boric acid and 9 parts of maltodextrin) and ground together in a mechanized ball mill over a period of about 1-10 hours, for example, about 3 hours, to prepare a first trituration of boric acid. The first triturated boric acid can be further triturated by mixing the first trituration with the carrier in a specified ratio, such as about 1:10, and repeating the above steps. The two-step trituration process falls within the practices of homeopathy system. An advantage of such homeopathic formulations is that they are acceptable for and can be used by the adherents to homeopathy.

In some embodiments of the processes for preparing the probiotic vaginal formulation, the formulation's ingredients other than boric acid may combined separately, forming a blend or a mixture lacking the boric acid. The boric acid component is then added in a separate step. For example, the probiotic, such as the probiotic comprising dried viable Lactobacillus cells, can be combined with at least a carrier and, optionally, other ingredients, such as one or more antioxidants (for example, vitamins C and/or E), to produce a blend comprising the probiotic, one or more antioxidants and a carrier. This blend, which includes at least the probiotic and the carrier and may also contain other components, such as one or more antioxidants, but does not include the boric acid component, can be referred to as "probiotic blend." The probiotic blend can be produced using various mixing procedures, one example of which is blending. Accordingly, the processes for preparing the probiotic vaginal formulations can contain a step of producing the probiotic blend, for example, by mixing or blending the probiotic with a carrier and, optionally, other specified components. Mixing or blending can be accomplished by any suitable process. For example, blending of the ingredients in a mechanized blender can be employed. Once produced, the probiotic blend is stored with minimal exposure to moisture, air and light, in order to preserve the viability of the probiotics in the blend. Standard manufacturing and quality control practices are used to avoid microbial contamination of the probiotic blend. The probiotic blend is combined with the boric acid component, such as triturated boric acid, in a separate step. For example, a specified amount of the probiotic blend can be mixed or blended with a specified amount of triturated boric acid, to prepare the probiotic vaginal formulation. Other components can also be incorporated during this step. Processes for preparing the probiotic vaginal formulations can include a different order of combining the formulations' components. For example, all the ingredients of the formulation can be combined by a suitable process, such as blending or mixing, in one step. In another example, boric acid and triturated, and the triturated boric acid is combined with the other formulation's ingredients in a single additional step. In another exemplary embodiment, the probiotic, such as the probiotic comprising dried viable Lactobacillus cells, can be combined with the carrier and boric acid ingredient (such as triturated boric acid) in one step, and the other ingredients, such as one or more antioxidants (for example, vitamins C and/or E) can be subsequently added in one or more steps. Other variations of the order of adding and mixing the ingredients are also possible. Mixing or blending can be accomplished by any suitable process, such as manual or mechanized blending. Once produced, the formulation should be stored with minimal exposure to moisture, air and light, in order to preserve the viability of the probiotics in the blend. Standard manufacturing and quality control practices are used to avoid microbial contamination of the formulation.

The probiotic vaginal formulations can be produced in various dosage forms. Accordingly, the processes for preparing the probiotic vaginal formulations may include one or more steps related to production of a dosage form. For example, if the probiotic vaginal formulation is in a capsule unit dosage form, the process for preparing the vaginal formulation can contain a step of filling a capsule with the composition containing the ingredients of the formulation, or equivalent steps. If the probiotic vaginal formulation is in a tampon unit dosage form, then the process for preparing the vaginal formulation may include a step of combining the composition containing the ingredients of the formulation with the material (such as a porous material), from which the tampon is produced, or equivalent steps. If the probiotic vaginal formulation is prepackaged in an applicator, then the process for preparing the vaginal formulation may include a step of packing the composition containing the ingredients of the formulation in the applicator (or filing the applicator with the composition), or equivalent steps.

Methods of Use

Processes for using the probiotic vaginal formulations are provided herein. For example, in some embodiments, the probiotic vaginal formulations are used to acidify or maintain the acidity of the vaginal environment. Accordingly, the probiotic vaginal formulations may be used in the methods of modulating acidification, including, increasing the acidity, maintaining the acidity, or lowering vaginal acidity or pH. In some embodiments, the probiotic vaginal formulations are used to establish or improve vaginal flora, for example, by increasing the levels of Lactobacilli in the vaginal flora or decreasing the levels of yeast, such as Candida yeast. The probiotic vaginal formulations may also be used in the methods of treating, alleviating, preventing or reducing the likelihood of urogenital infections or inflammatory conditions, including vaginitis, UTIs, vaginal atrophy and post-surgical inflammation in a subject. For example, the probiotic vaginal formulations may be used in the methods of treating, alleviating, preventing or reducing the likelihood of vaginitis or its symptoms, such as vaginal dryness, burning, or itching in a subject. In the context of the above methods, vaginitis may be various etiologies, such as, but not limited to, BV, yeast infection or vaginal atrophy. Vaginitis or vaginitis-related or vaginitis-like symptoms may also be of unknown etiology. In another example, the probiotic vaginal formulations may be used in the methods of treating, alleviating, preventing or reducing the likelihood of vaginal dryness of various etiologies, such as, but not limited to, BV, yeast infection, trauma, medication side-effect or vaginal atrophy. In another example, the probiotic vaginal formulations may be used in the methods of treating, alleviating, preventing or reducing the likelihood of urogenital inflammation, including vulvovaginal inflammation of various etiologies, such as, but not limited to, infection, irritation, trauma, such as post-surgical or childbirth trauma. One or more uses of the probiotic vaginal formulations may be described as suitable for improving, maintaining or achieving vaginal health.

Processes or methods of using the probiotic vaginal formulations include the step of vaginally administering to the subject a probiotic vaginal formulation in an effective amount. The effective amount may vary based on the desired effect, the specific formulation, the dosage form, the dosing regimen, and other factors. For example, the formulation, in capsule unit dosage form, may be administered in an amount of 1-5 capsules per day, including, for example, 1 or 2 capsules per day. The period of administration may be for at least 1 day, at least 3 days, at least 6 days, or as prescribed by a physician or until the improvement or reduction of the symptoms is achieved.= variation of the vaginal bacterial flora. BV etiology is not completely understood. Broad-spectrum antiobics, spermicides, hormones, and other factors may cause disruption of normal bacterial flora, leading to BV.

The noun "blend" is used herein to refer to a mixture of the solid ingredients of the compositions described herein. The terms "blend" and "mixture" can be used interchangeably. The verb "blend" is used to a process of mixing the ingredients or components of a composition to form a blend. The use of a blending machine (blender) is not required to obtain a blend.

Boric acid, also called boracic acid, orthoboric acid or acidum boricum, is an inorganic acid with the chemical formula $H_3BO_3$.

The term "capsule" is used herein in a pharmaceutical sense to refer to a hollow shell, in which one or more ingredients or components of a composition intended for administration to a subject are enclosed. Capsules can be hard-shelled or soft-shelled. Capsules are usually made from gelling agents, such as gelatin or plant polysaccharides or their derivatives, which dissolve upon administration. One example of a suitable plant polysaccharide is pullulan. pullulan, which is a linear polysaccharide composed primarily of repeating maltotriose units. The maltotriose units, which include three 1,4-linked glucose molecules, are linked by α-1,6-glycosidic bonds. An exemplary pullulan structure includes the following:

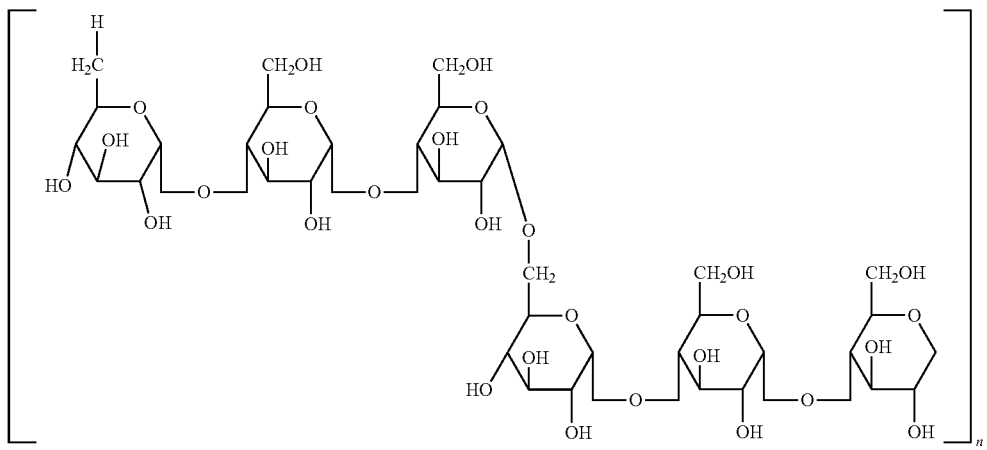

Definitions

The term "about," when used in combination with numerical values, is intended to encompass the range of ±10% of such numerical values The term "antioxidant" is used herein to refer to a substance that inhibits oxidation of other substances. Examples of antioxidants are vitamins A, C and E.

The term "bacterial vaginosis," abbreviated as "BV," and similar terms are to be understood in the broad sense as the alterations of vaginal bacterial flora composition in a female subject, as compared to a baseline, reference or "normal" vaginal bacterial flora composition. BV is not limited to a specific vaginal bacterial flora composition or any particular symptoms observed in a particular female subject or population of female subjects. While BV can manifest itself through a variety of symptoms, some of which are discussed elsewhere herein, BV can also be asymptomatic. BV is not necessarily accompanied by inflammation. In certain situations, BV may be considered a medical condition or disease, while in other situations BV may be viewed as a benign Besides gelling agents, capsules can also contain other ingredients, such as plasticizers, coloring agents (for example, titanium dioxide), preservatives or disintegrants.

The terms "carrier" and "excipient," as well as the related terms," may be used interchangeably to denote an ingredient or ingredients included in a formulation for the purpose of long-term stabilization, bulking up, dilution of other ingredients or for conferring enhancement of the properties of the composition, such as facilitating adsorption or improving solubility or disintegration. An excipient or a carrier can be described as an "inactive" or "inert" ingredient, but it is to be understood that even an excipient or a carrier characterized as "inactive" can play a role, sometimes significant, in dosage form performance.

The terms "dosage form," "unit dosage form" or "unit dosage," as well as the related terms, are used herein in to refer to a form or a configuration in which a composition or a formulation is provided for administration to a subject. One example of a dosage form is a "capsule unit dosage form," meaning a dosage form in which specified amounts of the composition's ingredients (including active ingredients, inactive ingredients or excipients, preservatives, etc.) are packaged in a capsule suitable for a single dose administration (such as oral or vaginal administration) to a subject. Multiple dosage forms can be administered to a subject over time in a selected dosing regimen.

The term "dried," when used in reference to bacterial cells, such as Lactobacillus cells, is used herein to denote bacterial cells with lowered moisture content, including bacterial cells free or substantially free from moisture. The terms "dehydrated" and "desiccated" can be used interchangeably with "dried." Dried bacterial cells can be obtained by subjecting bacterial cells to a drying process. A drying process may be used to produce dried viable bacteria suitable for long-term storage or incorporation into various products and formulations. It is to be understood that the term "dried," when used in reference to bacterial cells, is not limited by any particular drying process. One common process for drying bacterial cells is freeze-drying or lyophilization. Bacterial lyophilization protocols vary widely, but the following step are typically used in a lyophilization process: freezing of the sample, application of a high vacuum, warming of the sample while under vacuum which causes water sublimation, driving off excess water through a drying phase, and sealing of the sample to prevent water uptake. Bacteria can also be dried by processes other than lyophilization. For example, drying at temperatures above zero under vacuum can be used to produce dried viable bacterial cells. A bacterial sample used for drying is typically prepared by growing bacterial culture, for example, to late log or early stationary phase in a medium of choice and then harvesting the cells. If a broth culture is used, the cells can be suspended by centrifuging and then resuspended in a smaller volume of the same growth media or supplements prior to trying. The culture can also be dried without resuspension. In any event, in addition to the bacterial cells, the sample subjected to drying to produce dried viable bacterial cells may contain growth media ingredients, bacterial metabolites, bacterial cell debris, etc. The resulting dried sample may also contain these components, in a dried state.

The terms "effective amount" or "effective dose" are used herein to refer to an amount of a composition that produces a desired effect in at least a fraction of the subjects, to whom the composition is administered. The dose is further selected to avoid or minimize undesirable side effects.

"Fill weight" refers to the weight of the capsule unit dosage form formulation, as filled in a capsule.

The term "formulation" is used herein to denote a composition or a dosage form intended for administration to a subject and prepared according to a specified recipe, containing specified amounts of ingredients and/or prepared according to a specified procedure.

The terms "invention," "the invention," "this invention" and "the present invention," as used herein, are intended to refer broadly to all of the subject matter of this patent application and the claims below. Statements containing these terms should be understood not to limit the subject matter described herein or to limit the meaning or scope of the patent claims below.

The terms "lactic acid bacteria" (LAB) or Lactobacillales refer to a Glade of gram-positive bacteria that produce lactic acid as the major metabolic end product of carbohydrate formation. LAB include the genera of Lactobacillus, Leuconostoc, Pediococcus, Lactococcus and Streptococcus. Lactobacilli are abundant in the environment and inhabit bodies of humans and animals as commensals. L. acidophilus, L. crispatus, L. delbruekii, L. gasseri and L. iners are commonly found in healthy vaginal microflora. Lactobacillus gasseri is a species in the genus Lactobacillus that a normal inhabitant of the lower reproductive tract in healthy female subjects. Exemplary strains of L. gasseri include those deposited as having American Type Culture Collection (ATCC) accession number (ATCC No.) 33323, ATCC No. 19992, ATCC No. 4484, ATCC No. 4479, ATCC No. 4481, ATCC No. 4483, ATCC No. 4480, ATCC No. 4962, ATCC No. 9857, ATCC No. 4963, ATCC No. 29601, ATCC No. 33323. One exemplary strain of L. gasseri is L. gasseri JPS. Lactobacillus casei is a species of genus Lactobacillus widely used for dairy product fermentation. Exemplary strains of L. casei include a strain having ATCC accession number PTA-3945, which can also be referred to as L. casei KE01 or L. casei KE99. L. casei PTA-3945 is described in U.S. Pat. No. 6,797,266. Additional exemplary strains include ATCC No. 393, ATCC No. 334, ATCC No. 4007, ATCC No. 39539, ATCC No. 27139, ATCC No. 4940, ATCC No. 39392, ATCC No. 4913, ATCC No. 4646, ATCC No. 15008, ATCC No. 334D-5, ATCC No. PTA-2662, ATCC No. 55825, ATCC No. 55826, ATCC No. 55841, ATCC No. PTA-5149, ATCC No. 7469, ATCC No. 25598, ATCC No. 27216, ATCC No. 25599, ATCC No. 25302, ATCC No. 11582, ATCC No. 11982, ATCC No. 39595, ATCC No. 25180, ATCC No. 11578, ATCC No. 9595, ATCC No. 14435, ATCC No. 12116, ATCC No. 25303, ATCC No. 13075, ATCC No. 29599, ATCC No. 27092, ATCC No. 11981, ATCC No. 27773, ATCC No. 8530, ATCC No. 49178, ATCC No. 335, ATCC No. 14957, ATCC No. 7469a, ATCC No. HB-12558, ATCC No. HB-12560, ATCC No. HB-12559, ATCC No. 15820, ATCC No. 27792, ATCC No. 25937, ATCC No. 27092-B1, ATCC No. 87074. Lactobacillus acidophilus is a species of genus Lactobacillus that occurs naturally in the gastrointestinal tract of humans and animals and is a part of normal vaginal flora. Some strains of Lactobacillus acidophilus are used in dairy production. Exemplary Lactobacillus acidophilus strains are ATCC No. 4356, ATCC No. 3154, ATCC No. 53544, ATCC No. 53544, ATCC No. 43121, ATCC No. PTA-4482, ATCC No. 4796, ATCC No. 53546, ATCC No. 4355, ATCC No. 9224, ATCC No. 4357, ATCC No. 832, ATCC No. 4357D-5, ATCC No. PTA-6751, ATCC No. 6820.

"Maltodextrin" is a polysaccharide produced from starch by partial hydrolysis. Maltodextrin is usually found as a white hygroscopic spray-dried powder and consists of D-glucose units connected by alpha($1 \rightarrow 4$) glycosidic bonds connected in chains of variable length.

The term "probiotic" refers to live or viable microorganisms which, when administered in effective amounts to a subject, confer a health benefit on the subject. For example, the probiotics included in the probiotic vaginal formulations described herein, which are suitable for vaginal administration to female subjects, may improve the subjects' vaginal health. The term "probiotic," as used herein, encompasses live microorganisms as well as viable microorganisms in dormant states, including frozen microorganisms, desiccated or dried microorganisms, spores, cysts or microorganisms in various states of reduced metabolic activity, which can be reconstituted upon exposure to suitable conditions.

The term "subject" is used herein to describe a human or an animal. In the context of the embodiments of the present products, formulations, and processes, "subject" denotes a female mammal, such as a human, to whom the compositions are vaginally administered. Female subjects can have or be at risk of developing a particular disease or condition, for example, a urogenital infection, such as vaginitis. For example, female subjects may be at risk of recurrence of a urogenital infection or vaginitis, based on their medical history, antibiotic use, spermicide use or lifestyle (for example, sexual habits). Female subjects may also have or wish to prevent a urogenital infection or vaginitis or symptoms thereof, a suspected urogenital infection or suspected vaginitis, and urogenital infection-like or vaginitis-like symptoms, even in the absence of a formal diagnosis or full-blown urogenital infection or vaginitis.

The term "suppository" refers to dosage forms or formulations that are inserted into body cavities. Suppositories are solid bodies of various sizes and shape, which dissolve, disintegrate or melt upon administration. Suppositories can be provided in a variety of shapes and sizes. Vaginal suppositories are suitable for insertion into a vaginal cavity or urogenital tract, with or without an applicator. For example, vaginal suppositories can be inserted with an applicator high into the vaginal tract or with or without an applicator into the vaginal cavity. Vaginal suppositories are usually globular, oviform, or cone-shaped, but can be of any shape or size suitable for insertion into the vaginal cavity. A tablet, a ring or a capsule suitable for insertion into vaginal cavity or urogenital tract is included in the scope of the term "suppository."

The term "tampon" refers to a body made of an adsorbent material suitable for insertion into a vaginal cavity or urogenital tract, with or without an applicator. Tampons comprising a probiotic formulation can be used as a dosage form for delivery of the probiotic vaginal formulation.

The terms "trituration," "triturate" and the related terms are used herein to refer to a process of mixing components of a composition thoroughly, for example, by grinding one solid component with another solid component to dilute one of the components. Trituration may involve reducing particle size of the components.

The term "vaginal product" or "vaginal formulation" is used herein to refer to compositions of matter in a dosage form suitable for vaginal administration. The terms "probiotic vaginal product" and "probiotic vaginal formulation" refer to a composition of matter in a dosage form suitable for vaginal administration and comprising a probiotic. Some examples of vaginal formulations are suppositories (including, but not limited to, capsules and tablets), tampons, solutions, powders, ointments, creams and aerosol foams.

"Vaginitis" is a vulvovaginal condition that can manifest itself in inflammation, discharge, itching and pain. Some types of vaginitis are bacterial vaginosis, yeast infection, trichomoniasis, which is caused by a parasite and is commonly transmitted by sexual intercourse, and vaginal atrophy (atrophic vaginitis), which results from reduced estrogen levels, for example, after menopause.

The term "vaginal administration" includes "transvaginal administration" and "intravaginal administration," which refer to routes of administration, in which a substance, a composition or a formulation is applied inside a vaginal cavity or vulvovaginal area or through the vagina to other parts of the urogenital tract.

The term "vaginal dryness" refers to lack of vaginal moisture, which can have different causes. For example, during menopause, the drop in estrogen levels reduces the amount of moisture available. Vaginal dryness can also be caused by a drop in estrogen levels due to childbirth and breastfeeding. radiation or chemotherapy treatment for cancer; surgical removal of the ovaries; anti-estrogen medications used to treat uterine fibroids or endometriosis. Some other non-limiting causes of vaginal dryness include Sjögren's syndrome (an autoimmune disorder), allergy and cold medications and certain antidepressants, douching, lack of foreplay before sexual intercourse.

The term "vaginal yeast infection" is used herein to refer to a condition caused by overgrowth of yeast in the vulvovaginal area. Vaginal yeast infections are usually caused by excessive growth of *Candida* yeast, such as, but not limited to, commensal organism *Candida albicans*. Other *Candida* species implicated in vaginal yeast infections include, but are not limited to, *Candida glabrata, Candida parapsilosis, Candida krusei* and *Candida tropicalis*. Vaginal yeast infection can be referred to as "vaginal candidiasis" or "candidal vaginitis." Vaginal yeast infections can also be caused by non-*Candida* yeast, such as *Trichosporon* species, such as *Trichosporon beigelii*, and *Sacharomyces cereviasae*. The symptoms of vaginal yeast infections are vaginal irritation, discharge and intense itchiness of the vagina and the vulva. As is the case with BV, broad-spectrum antibiotics, spermicides, hormones, and other factors, not yet fully understood, may cause disruption of normal bacterial flora, leading to vaginal yeast infections. Vaginal yeast infections are also common in immunocompromised subjects.

The term "viable" is used herein to describe live bacterial cells as well as the cells that are in a state of reduced metabolic activity (for example, dried cells) but are capable of growing and developing upon exposure to suitable conditions or environments, such as suitable laboratory culture conditions or a suitable natural environment. Viability of bacterial cells can be determined using various methods and assays and expressed in various ways. For example, a colony-forming unit (CFU) may be used to express viability of bacterial cells or group of cells. The assays quantifying viable bacterial cells in CFUs intend to count the cells capable of multiplying via binary fission under controlled culturing conditions. An example of a CFU counting assay is the standard plate assay, which can be performed manually or using an automated system.

The term "vitamin C" refers to L-ascorbic acid or its forms, such or ascorbate (anion of ascorbic acid) or ascorbic acid salts.

The term "vitamin E" refers to a group of compounds that include both tocopherols and tocotrienols. One of such compounds is alpha-tocopherol and related compounds, one of which is DL-alpha-tocopherol acetate.

The term "urinary tract infection" (UTI) is an infection that affects part of the urinary tract. UTI affecting lower urinary tracts may be referred to as a bladder infection or cystitis. Symptoms from a lower urinary tract include pain with urination, frequent urination, and feeling the need to urinate despite having an empty bladder.

The term "urogenital infection" is an umbrella term used to refer to a condition of urinary and/or genital tract that is, at least in part, caused by microorganisms. Urogenital infections include BV, UTIs and vaginal yeast infections. Urogenital infections can have various etiologies, related, for example, to sexual practices, use of spermicides or antibiotics, douching, or other things. For example, pathogens may be transferred from the rectum to the vagina and/or the bladder.

The term "urogenital inflammatory conditions," which can be encompassed by the expression "urogenital infection and inflammatory conditions" may be used in singular or plural and is an umbrella term used to refer to inflammation occurring in urinary and/or genital tract, including vaginal or vulvovaginal inflammation. The term "urogenital inflammatory conditions" can be used interchangeably with the term "urogenital inflammation" and is not limited by the cause of the inflammation. Some non-limiting causes of urogenital inflammation are as follows: chemical irritation to the lining of the genitals, such as from soaps, bubble bath, or laundry detergent; urogenital infections, including sexually transmitted infections and other infections, such as vaginal yeast infections and UTIs, pelvic inflammatory disease, and cervical infections; ulceration of the cervical lining; trauma, which may be caused by childbirth, surgery, intercourse, tampon insertion, or speculum insertion during a pelvic exam, tumors, growths, or cancer; inadequate lubrication prior to intercourse; medications, including hormones, antibiotics, antihistamines; hormone changes or imbalances; autoimmune disorders; tight-fitting clothing.

EXAMPLES

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Homeopathic Boricum Acidum 2× Preparation

Homeopathic boricum acidum (Homeopathic Boricum Acidum 2×) with maltodextrin as a filler was prepared according to the trituration procedure described below. Maltodextrin used for preparation of Homeopathic Boricum Acidum 2× was sourced from Grain Processing Corporation, Muscatine, Iowa, as Maltrin QD® 500. Boric acid used for preparation of Homeopathic Boricum Acidum 2× was sourced from Science Company (Lakewood, Colo.). Boric acid complied with the requirements of the Homeopathic Pharmacopoeia of the United States (HPUS) (available online).

Boricum Acidum 2× Trituration Procedure
1. Weigh 1 part of boric acid and 9 parts of maltodextrin. Mix boric acid and maltodextrin together carefully and pour into the ball mill jar for grinding.
2. Fill the ball mill jar with the grinding balls and tightly cover the jar with its lid.
3. Place the closed jar in the ball mill and turn on the motor. Allow the ball mill jar to rotate and grind the mixture for at least 3 hours or until the mixture becomes very fine.
4. Remove the mixture from the jar. This is 1× dilution mixture of boric acid.
5. Prepare a 2× dilution of boric acid by weighing 1 part of the 1× dilution mixture of boric acid and 9 parts of maltodextrin.
6. Mix 1× dilution mixture of boric acid and maltodextrin together carefully and pour the into the ball mill jar.
7. Repeat Steps 3-5.
8. Remove the resulting Homeopathic Boricum Acidum 2× from the ball jar, place in a suitable container and seal tightly.

Example 2

Probiotic Blend Preparation

The Probiotic Blend (PB) containing two lactic acid probiotic bacteria, such as *Lactobacillus casei* KE99 and *L. gasseri* JPS, antioxidants, such as Vitamins C and E, and maltodextrin, was prepared according to the procedure described below. Maltodextrin was sourced from Grain Processing Corporation (Muscatine, Iowa) as Maltrin QD® 500. The probiotic bacterial products were purchased from ProbioFerm (Des Moines, Iowa) as a dry, solid powder (the details are provided below). Ascorbic acid was sourced from Shandong Tianli Pharmaceutical Co. Ltd. (Shouguang City, Shandong Province, Conn.) as Ascorbic Acid USP 100%. Encapsulated vitamin E was sourced from Green Wave Ingredients (La Mirada, Calif.) as Vitamin E 50% SD CWS Powder (contains 50% by weight of DL-alpha tocopherol acetate).

According to the specification sheet and other information provided by ProbioFerm, *L. gasseri* product "*Lactobacillus gasseri* 100 Billion" used for preparation of PB contained, as supplied, 60% of dried *L. gasseri* JPS fermentation culture, 40-50% maltodextrin and 1% silica, all by weight The product, as supplied, contained >100 billion CFU/g bacteria, <100 CFU/g mold/yeast. The product was negative for coliform group bacteria, had water activity of <0.35, and had an appearance of fine white to light yellow dry granular powder. *L. gasseri* product was stored at 4° C. or less prior to preparation of PB.

According to the specification sheet and other information provided by ProbioFerm, *L. gasseri* product "*Lactobacillus gasseri* 50 Billion" used for preparation of PBB contained, as supplied, 50-60% of dried *L. gasseri* JPS fermentation culture, 40-50% maltodextrin and 1% silica, all by weight. The product, as supplied, contained >50 billion CFU/g and <100 CFU/g mold/yeast. The product was negative for coliform group bacteria, had water activity of <0.35, and had an appearance of fine white to light yellow dry granular powder. *L. gasseri* product was stored at 4° C. or less prior to preparation of PB.

According to the specification sheet and other information provided by ProbioFerm, *L. casei* product "*Lactobacillus casei* KE99 200 Billion" used for preparation of PBB contained, as supplied, 50-60% of dried *L. casei* KE99 fermentation culture, 40-50% maltodextrin and 1% silica, all by weight. The product, as supplied, contained >200 billion CFU/g bacteria and <100 CFU/g mold/yeast. The product was negative for coliform group bacteria, had water activity of <0.35, and had an appearance of fine white to light yellow dry granular powder. *L. casei* product was stored at 0° C. or less prior to preparation of PB.

Probiotic Blend Preparation Procedure
1. Weigh ascorbic acid, Vitamin E and maltodextrin and pour them into a blender bin of a blending machine.
2. Weigh a combination of *L. casei* product (such as "*Lactobacillus casei* KE99 200 Billion," Probioferm) and *L. gasseri* product ("*Lactobacillus* gasseri 100 Billion" or "*Lactobacillus* gasseri 50 Billion," Probioferm) and add them into the blender bin.
3. Using a blending machine (BOHLE PM1000) blend the mixture obtained in step 10 for approximately one (1) hour, resulting in PB.
4. When the blending step is completed, take quality control (QC) samples of PB for testing as needed. Conduct QC testing using QC PB Uniformity Testing, Assays of Vitamin C and E, Probiotic Enumeration and Microbial Testing such as Aerobic Plate Count, Yeast and Mold Count and Test for Presence of *E. coli, Salmonella* and *S. aureus*. QC procedures to be conducted substantially as described in Food and Drug Administration's (FDA's) Bacteriological Analytical Manual (BAM), which presents the agency's preferred laboratory procedures for microbiological analyses of foods and cosmetics.

Example 3

Preparation of the Blend of Boricum Acidum 2× and Probiotic Blend ("Final Blend")

The Final Blend containing, by weight, 0.059-0.072% Homeopathic Boricum Acidum 2× and 99.928%-99.941% PB, was prepared according to the following procedure.

Final Blend Preparation Procedure
1. Weigh the required amounts of Homeopathic Boricum Acidum 2× and PB and pour them into a V-Blender.
2. Blend for a minimum of 30 minutes.
3. Unload the final blend in a suitable container and seal tightly.
4. Take QC samples of the final blend for testing. The testing procedures are described in the previous example.

Example 4

Preparation of Capsule Unit Dosage Form

Capsule unit dosage form was prepared by encapsulating the Final Blend of Homeopathic Boricum Acidum 2× and PB. The capsules used in preparation of the capsule unit dosage form were obtained from Capsugel (Morristown, N.J.) and were composed of pullulan and titanium dioxide. The capsule type was carefully selected for optimal vaginal delivery of the final blend. Encapsulation was performed according to the following procedure.

Encapsulation procedure
1. Set the encapsulating machine (Bosch GKF 1200) to fill each capsule with 380 mg±7% of the final blend.
2. Take the average weight of 10 empty capsules for weight verification.
3. Run the encapsulation machine to fill the capsules.
4. Pack filled capsules in a suitable container.
5. During the run, take samples of filled capsules every 30 minutes for visual inspection of appearance, fill weight and capsule length.
6. Take QC samples of capsule unit dosage form as needed. Some of the testing protocols used were Weight Variation, Content Uniformity, Disintegration, Lactobacillus Enumeration and Microbial Testing for Aerobic Plate Count, Yeast and Mold Count, Test for Presence of E. coli, Salmonella and S. aureus.

TABLE 1

Content of Homeopathic Boricum Acidum 2X in the probiotic vaginal product

| Homeopathic Boricum Acidum 2X Ingredient | Nominal amount per capsule unit dosage form, (mg per capsule) | Fill Weight %, probiotic vaginal product (does not take into account capsule weight) | |
|---|---|---|---|
| | | Nominal | Range |
| boric acid | 0.0250 | 0.0066 | 0.0059-0.0072 |
| maltodextrin (derived from Homeopathic Boricum Acidum 2X) | 0.2250 | 0.0591 | 0.0532-0.0650 |

TABLE 2

Content of PB ingredients in the probiotic vaginal product

| Ingredient | Nominal amount per capsule unit dosage form, (mg per capsule) | Weight %, probiotic vaginal product (as supplied) | |
|---|---|---|---|
| | | Nominal | Range |
| Ascorbic acid | 49.9993 | 13.1404 | 11.83-14.45 |
| Vitamin E 50% SD CWS Powder* | 148.0002 | 38.8962 | 35.01-42.79 |
| Lactobacillus casei KE99 200 Billion | 9.9994 | 2.6280 | 2.37-2.89 |
| Lactobacillus gasseri 100 Billion** | 6.5930 | 1.7327 | 1.56-1.91 |
| Lactobacillus gasseri 50 Billion** | 6.8128 | 1.7905 | 1.61-1.97 |
| Maltrin QD 500 (maltodextrin)*** | 158.8453 | 41.7465 | 37.57-45.92**** |

*This is a microencapsulated form of Vitamin E, provided as a powder and containing 50% of DL-alpha-tocopherol by weight.
**One or both of of "Lactobacillus gasseri 100 Billion" or "Lactobacillus gasseri 50 Billion" may be included to achieve the goal amount of viable bacterial cells per capsule
**derived from PB
***total maltodextrin content range (accounting for maltodextrin derived from Homeopathic Boricum Acidum 2X, was 37.62-45.99%

Example 5

Probiotic Vaginal Product

Tables 1-2 illustrate the composition of the probiotic vaginal formulation prepared according to the procedures described in the previous examples. The probiotic vaginal formulation is the encapsulated final blend (capsule unit dosage form) containing 380 mg±7% of the final blend in each capsule.

Example 5

Probiotic Vaginal Product Variant

Tables 3 and 4 illustrate the composition of the probiotic vaginal formulation prepared according to the procedures described in the previous examples.

TABLE 3

Content of the selected ingredients in the probiotic vaginal product variant

| Ingredient | Amount per capsule |
|---|---|
| Aloe Vera Extract | 100 mg |
| Ascorbic Acid | 50 mg |
| Vitamin E 50% SD CWS Powder* | 148 mg |
| Lactobacillus casei KE99 200 Billion CFU/g | 10 mg |
| Lactobacillus gasseri JPS* | 10 mg |
| Maltrin QD 500 | 60 mg |

*Total amount of one or both of Lactobacillus gasseri JPS 100 Billion CFU/g and Lactobacillus gasseri JPS 50 Billion CFU/g to obtain 1 billion CFU per capsule of L. gasseri.

TABLE 4

Content of the selected ingredients in the probiotic vaginal product variant

| Ingredient | Amount per capsule |
| --- | --- |
| Ascorbic Acid | 50 mg |
| Vitamin E 50% SD CWS Powder* | 148 mg |
| Lactobacillus casei KE99 200 Billion CFU/g | 10 mg |
| Lactobacillus gasseri JPS 100 Billion CFU/g* | 10 mg** |
| Lactobacillus gasseri JPS 50 Billion CFU/g* | |
| Maltrin QD 500 q.s. to make 378 mg/serving | 156.594 mg |

**Total amount of one or both L. gasseri components to obtain 1 billion CFU per capsule of L. gasseri.

Example 6

Probiotic Vaginal Product Testing

In-vitro testing of probiotic vaginal product was conducted using a solution of simulated vaginal fluid (SVF) (see, e.g., Margues et al., Simulated Biological Fluids with Possible Application in Dissolution Testing, Dissolution Technologies (August 2011)) adjusted to pH 7.0 with potassium hydroxide solution and warmed to 37° C. (simulating the body temperature). One capsule of the probiotic vaginal product was added to the solution while the pH-meter electrode was dipped into the solution. Disintegration of the capsule started in less than 5 minutes. At 5 minutes after the capsule disintegrated (per visual determination), the pH of the solution dropped to 4.5. After the addition of another capsule to the solution and the capsule's disintegration (per visual determination), the pH of the solution dropped further to 4.3. The pH reading remained constant for over 2 hours.

All patents, patent applications, publications, and abstracts cited above are incorporated herein by reference in their entirety. Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention as defined in the following claims.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

The invention claimed is:

1. A method of alleviating symptoms of vaginal atrophy in a female subject having the vaginal atrophy, comprising vaginally administering to the female subject a formulation comprising an effective amount of a composition comprising dried viable cells of Lactobacillus casei, dried viable cells of Lactobacillus gasseri, triturated boric acid and a carrier.

2. The method of claim 1, wherein the formulation is a suppository, a capsule, a tablet, a tampon or a component of a kit comprising an applicator.

3. The method of claim 1, wherein the female subject has at least one of vaginal dryness, vaginal burning, or vaginal itching.

4. The method of claim 1, wherein the formulation is self-administered by the female subject.

5. The method of claim 1, wherein the triturated boric acid is in homeopathic form.

6. The method of claim 1, wherein the dried viable cells of Lactobacillus casei comprise dried viable cells of Lactobacillus casei strain ATCC PTA-3945.

7. The method of claim 1, wherein a dosage form of the formulation comprises about 0.0059-0.0072% by weight of boric acid, about 1.8-3.3 billion CFU of Lactobacillus casei, and about 0.9-2.2 billion CFU of Lactobacillus gasseri.

8. The method of claim 1, wherein the formulation further comprises a component prepared from a media in which Lactobacillus cells were cultured.

9. The method of claim 1, wherein the formulation further comprises dried viable cells of Lactobacillus acidophilus.

10. The method of claim 1, wherein the formulation comprises up to 600 mg of triturated boric acid.

11. A method of alleviating vaginal dryness in a female subject having the vaginal dryness, comprising vaginally administering to the female subject a formulation comprising an effective amount of a composition comprising dried viable cells of Lactobacillus casei, dried viable cells of Lactobacillus gasseri, triturated boric acid and a carrier.

12. The method of claim 11, wherein the formulation is a suppository, a capsule, a tablet, a tampon or a component of a kit comprising an applicator.

13. The method of claim 11, wherein the female subject has at least one of bacterial vaginosis, yeast infection, trauma, or vaginal atrophy.

14. The method of claim 11, wherein the formulation is self-administered by the female subject.

15. The method of claim 11, wherein the triturated boric acid is in homeopathic form.

16. The method of claim 11, wherein the dried viable cells of Lactobacillus casei comprise dried viable cells of Lactobacillus casei strain ATCC PTA-3945.

17. The method of claim 11, wherein a dosage form of the formulation comprises about 0.0059-0.0072% by weight of boric acid, about 1.8-3.3 billion CFU of Lactobacillus casei, and about 0.9-2.2 billion CFU of Lactobacillus gasseri.

18. The method of claim 11, wherein the formulation further comprises a component prepared from a media in which Lactobacillus cells were cultured.

19. The method of claim 11, wherein the formulation further comprises dried viable cells of Lactobacillus acidophilus.

20. The method of claim 11, wherein the formulation comprises up to 600 mg of triturated boric acid.

* * * * *